United States Patent [19]

Leach

[11] 3,994,982

[45] Nov. 30, 1976

[54] PROCESS FOR DIRECT METHYLATION OF PHENOL IN LIQUID PHASE

[75] Inventor: Bruce L. Leach, Ponca City, Okla.

[73] Assignee: Continental Oil Company, Ponca City, Okla.

[22] Filed: Aug. 25, 1975

[21] Appl. No.: 607,731

[52] U.S. Cl. .......................... 260/621 R; 260/624 C
[51] Int. Cl.² .......................................... C07C 39/06
[58] Field of Search ......... 260/621 R, 624 C, 624 R

[56] References Cited
UNITED STATES PATENTS

| | | | |
|---|---|---|---|
| 3,290,389 | 12/1966 | Hahn | 260/624 C |
| 3,367,981 | 2/1968 | Napolitano | 260/624 C |
| 3,422,156 | 1/1969 | Thoma | 260/621 R |
| 3,426,358 | 2/1969 | Schlichting et al. | 260/621 R |
| 3,624,163 | 11/1971 | Del Bel | 260/621 R |
| 3,670,030 | 6/1972 | Sparks | 260/624 C |
| 3,707,569 | 12/1972 | Van Sorge | 260/621 R |
| 3,737,466 | 6/1973 | Sharp et al. | 260/621 R |

*Primary Examiner*—James O. Thomas, Jr.
*Assistant Examiner*—W. B. Lone
*Attorney, Agent, or Firm*—Cortlan R. Schupbach, Jr.

[57] ABSTRACT

Phenol is directly methylated in liquid phase while in the presence of gamma aluminas derived from Ziegler alcohol synthesis. The reaction is carried out continuously in liquid phase at temperatures of from about 300° to 400° C, liquid hourly space velocities of from about 1.0 to 15.0, pressures of from 500 to 1500 pounds per square inch gauge and a methylating agent to phenol mol ratio of from about .1 to about 3.0. High selectivity and yield of desired products such as ortho cresol, 2,6-xylenol and 2,3,6-trimethylphenol is obtained, while minimizing m,p cresol formation.

2 Claims, No Drawings

PROCESS FOR DIRECT METHYLATION OF PHENOL IN LIQUID PHASE

This invention relates to the liquid phase methylation of phenol. More specifically, this invention relates to the liquid phase methylation of phenol to produce 2,6-xylenol, 2,3,6-trimethylphenol and ortho cresol.

2,6-xylenol is useful as a precursor to 2,3,6-trimethylphenol and other useful products. 2,6-xylenol also finds uses in polymer and plastics applications such as that described in U.S. Pat. No. 3,446,856. 2,3,6-trimethylphenol is useful as an intermediate in Vitamin E synthesis. Ortho cresol is useful in chemical applications as an intermediate, for example as a precursor to 6-chloro-2-methyl phenol which is an intermediate in the synthesis of herbicides. Other uses are well known to those skilled in the art.

Many types of aluminum oxide catalysts are known in the art. Of these, gamma aluminas are preferred for many reactions involving phenols both in the vapor and liquid phase. Normally, these reactions are carried out by reacting phenol and olfins to introduce hydrocarbon groups onto the aromatic ring of a phenol. Representative examples of such patented processes are U.S. Pat. Nos. 3,290,389 issued to Hahn; 3,367,981 issued to Napolitano; 3,542,750 issued to Tomomatsu; 2,450,766 issued to Nixon et al.; U.S. Pat. No. 3,670,030 issued to Sparks; and British Patent No. 1,102,309. These processes together or singly teach reacting phenols with olfins in the presence of a gamma alumina for purposes such as polymerizing cyclic alkaline oxides, introducing hydrocarbon groups onto rings of a phenol and production of phenols alkylated in an ortho position.

Purification of the major products of these and similar reactions has been a problem. This is especially true when 2,6-xylenol is produced along with m,p cresols, due to the great similarity in boiling points of these compounds. m,p Cresol production greatly increases at temperatures over 400° C. It would be greatly desirable to have direct methylation of phenol under conditions which minimize formation of undesirable by-products while forming desirable products.

It is therefore an object of the present invention to provide an improved process for the liquid phase direct methylation of phenol to produce 2,6-xylenol, ortho cresol, and 2,3,6-trimethylphenol. Other objects will become apparent to those skilled in this art as the description proceeds.

In accordance with the present invention, an improved process for selectively producing 2,6-xylenol, 2,3,6-trimethylphenol, and ortho cresol by the liquid phase direction methylation of phenol in the presence of a gamma alumina derived from a Ziegler alcohol process is provided. The process is an improvement over the heretofore known processes in several regards giving unexpected results. High conversion of the phenol and high selectivity to the desired products are obtained without resorting to more severe reaction conditions with a resultant decrease in undesirable by-products. The selectivity is surprising since aluminas derived from the aluminum alkoxide hydrolysis process are much superior to other aluminas although all can be classified as gamma aluminas. The catalyst of the present invention is more active than other gamma aluminas, allowing lower reaction temperatures for which produces fewer m,p cresols.

Concisely, the improved process of the present invention comprises (a) reacting phenol with a methylating agent in the liquid phase (b) at a temperature of from about 300° to about 400° C, (c) at a liquid hourly space velocity of from 0.1 to about 15.0 (d) at a pressure of from about 500 to about 1500 pounds per square inch gauge (e) at a mol ratio of about 0.1 to about 3.0 (f) while in contact with a gamma alumina catalyst derived from aluminum alkoxide hydrolysis.

In carrying out the process of the present invention, from about 0.1 to about 0.3 mols of methanol or other methylating agents such as isobutylene are used per mol of phenol, but from about 0.2 to about 1.0 mols are preferred. Methanol is preferred as a methylating agent. Temperatures of from 370° to 390° C are preferred in order to reduce the amount of undesirable m,p cresol formed. Liquid hourly space velocity (LHSV) of from about 2 to about 8 is most preferred. Pressures of from about 600 to about 1,000 pounds per square inch gauge are also preferred.

The process of the present invention can be carried out efficiently in a batch reactor or a continuous flow reactor. Of these, the continuous flow reactor is preferred. In the continuous flow reactor, the alumina catalyst is suitably divided and placed in a position to catalyze the reaction between the phenol and the methylating agent. The reactor flow can be either upward or by gravity, however, gravity flow is preferred.

The gamma aluminas of the present invention are surprisingly efficient in a methylating phenol. While the reason is not known, aluminas derived from aluminum alkoxide hydrolysis have been discovered to produce superior results when compared to aluminas obtained from other sources. Examples of such desired aluminas are CATAPAL aluminas and DISPAL aluminas sold by Continental Oil Company. These aluminas, which preferentially absorb methanol, appear to show enhanced reactivity in liquid phase reactions. In contrast, other prior art gamma aluminas do not show the conversion nor the selectivity to the desired products.

When comparative runs are carried out under the same reaction conditions, the catalyst of the present invention produce significantly higher yields and selectivities. 2,3,6-trimethylphenol, while in minor proportion, is an extremely useful product and can be recovered using conventional methods such as fractional distillation and/or recrystallization. Heavier materials produced can be removed by fractional distillation.

Major preferred products, such as ortho cresol, can be recovered at about 35 weight percent yield; 2,6-xylenol at about 12 percent yield; and 2,3,6-trimethylphenol at about 1.75 percent yield based on total reactant weight. The catalyst of the present invention, while exceptionally effective, also produced larger amounts of by-products. These by-products, however, are not excessive and can be either recycled, recovered, or discarded without undue effort. By-products which are especially undesirable, such as m,p cresol, are produced in lower by-product/product ratio.

The invention is more concretely described with reference to the example below wherein all parts and percentages are by weight unless otherwise specified. The example is intended to illustrate the invention and not to limit it.

The data disclosed herein was generated using a three-eighths inch stainless steel reactor containing one-sixteenth inch diameter alumina extradite. Flow in the reactor could be varied either upward or by gravity.

The reactor contained approximately 5 cubic centimeters of catalyst. Catalysts used were designated by A, B, and C. Catalyst A was CATAPAL SB alumina sold by Continental Oil Company. Catalyst B was Harshaw AL-1404T sold by Harshaw Chemical Company. Catalyst C was Harshaw HA-200 sold by Harshaw Chemical Company. All catalysts were screened through 10 to 28 mesh. All catalysts classify as gamma aluminas. The reactor was heated using an electric furnace. The temperature was measured in the center of the reactor by a thermocouple. No cooling was provided. After leaving the reactor, the product stream was condensed and product distribution was determined using gas liquid, chromatograph (GLC). Actual percentages or products were measured using a computerized program which measured the area under the GLC curve.

EXAMPLE

A mixture of phenol and methanol (0.7 mol ratio methanol:phenol) was pumped at a liquid hourly space velocity of 3.0 through alumina catalyst in a ⅜ inch tubular reactor. The temperature was 350° C. 500 pounds per square inch back pressure was maintained. The results are shown in Table I below.

TABLE 1

COMPARISON OF REACTIVITY FOR LIQUID PHASE PHENOL METHYLATION

| Component | Feed | CATALYST | | |
|---|---|---|---|---|
| | | A | B | C |
| Methanol (Dimethylether) | 19.24 | 0.39 | 7.29 | 17.52 |
| Anisole | | 0.86 | 16.62 | 11.43 |
| Phenol | 80.76 | 47.03 | 50.56 | 67.33 |
| o-Me Anisole | | 0.24 | 1.70 | 0.04 |
| o-Cresol | | 34.64 | 20.44 | 3.64 |
| m,p-Cresol | | 0.24 | 0.17 | 0.02 |
| 2,6-Xylenol | | 11.99 | 2.94 | 0.03 |
| 2,4/2,5 | | 1.09 | 0.10 | |
| 3,5/2,3 | | 0.58 | 0.05 | |
| 2,4,6-Trimethylphenol | | 0.33 | | |
| 2,3,6-Trimethylphenol | | 1.83 | 0.06 | |
| 2,3,5/2,4,5-Trimethylphenol | | 0.03 | | |
| Pentamethylbenzene | | 0.08 | | |
| 2,3,4,6/2,3,5,6 Trimethylphenol | | 0.46 | 0.02 | |
| Hexamethylbenzene | | 0.04 | | |
| Pentamethylphenol | | 0.14 | | |

Distribution using the aluminas of the present invention is clearly slanted toward desirable products with a decrease in the ratio of m,p cresol by-products. Over 400 percent increase in 2,6 xylenol was found with only a 70 percent increase in undesirable m,p cresol. All aluminas used were gamma aluminas. The Harshaw aluminas were derived respectively from the sodium aluminate and alum processes. The Catapal SB alumina was derived from Ziegler alcohol synthesis process.

The alumina which is a by-product of the Ziegler alcohol process is an alpha alumina monohydrate, which is then heated at 450° to 500° C to form an anhydrous gamma alumina. During the reactive of the present invention, the anhydrous gamma alumina is somewhat rehydrated due to the water formed during the methylation and the pressure under which the reaction is carried out.

The reason for the enhanced reactivity and selectivity of this particular catalyst is not known.

It can be seen that the present invention gives high selectivity to the desired products without increasing severity of reaction conditions. It will be apparent that the improved process is much superior than those provided by the prior art.

While certain embodiments and details have been shown for the purpose for illustrating this invention, it will be apparent to those skilled in this art that various changes and modifications may be made herein without departing from the spirit or the scope of the invention.

I claim:

1. In a process for the continuous liquid phase methylation of phenol to produce 2,6-xylenol, o-cresol, and 2,3,6-trimethylphenol while in the presence of a gamma alumina catalyst at a pressure of from about 500 pounds per square inch gauge to about 1500 pounds per square inch gauge, the improvement comprising:

a. using a gamma alumina derived from aluminum alkoxide hydrolysis,
   b. a methanol/phenol mol ratio of from about 0.1 to about 3.0,
   c. a liquid hourly space velocity of from about 1.0 to about 15.0, and
   d. a temperature of from about 300° C to about 400° C.

2. A process as described in claim 1 wherein the reaction is carried out at a liquid hourly space velocity of from about 2 to about 8; a pressure of from about 600 pounds per square inch gauge to about 1,000 pounds per square inch gauge and a mol ratio of from about 0.2 to about 1.0.

* * * * *